(12) United States Patent
Nakada et al.

(10) Patent No.: US 6,403,847 B1
(45) Date of Patent: Jun. 11, 2002

(54) PROCESS FOR PRODUCING 1,1,1,3,3-PENTAFLUORO-PROPANE AND/OR 1-CHLORO-3,3,3-TRIFLUOROPROPENE

(75) Inventors: Tatsuo Nakada; Takashi Shibanuma; Noriaki Shibata, all of Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/787,545

(22) PCT Filed: Aug. 4, 1999

(86) PCT No.: PCT/JP99/04243

§ 371 (c)(1),
(2), (4) Date: Mar. 20, 2001

(87) PCT Pub. No.: WO00/17136

PCT Pub. Date: Mar. 30, 2000

(30) Foreign Application Priority Data

Sep. 22, 1998 (JP) .............................. 10-267957

(51) Int. Cl.⁷ .......................... C07C 17/25; C07C 17/08
(52) U.S. Cl. ...................... 570/156; 570/153; 570/165; 570/166; 570/167; 570/168; 570/169
(58) Field of Search ................... 570/167, 166, 570/165, 168, 169, 153, 156

(56) References Cited

U.S. PATENT DOCUMENTS 5,574,192 A * 11/1996 Van Der Puy .............. 570/167

* cited by examiner

*Primary Examiner*—Alan Siegel
(74) *Attorney, Agent, or Firm*—Armstrong, Westerman & Hattori, LLP

(57) ABSTRACT

One or more materials selected from 1,1,1,3,3-pentachloropropane, 1,1,3,3-tetrachloropropene and 1,3,3,3-tetrachloropropene are used as the specific materials described above. Before submitting the materials and HF to a fluorination reaction, almost all water is removed from them.

To continuously manufacture useful intended products efficiently as well as to prevent deactivation of the catalyst and the accumulation of organic substances with high boiling points when manufacturing said useful 1,1,1,3,3-pentafluoropropane and/or 1-chloro-3,3,3-trifluoropropene, by fluorinating the specific materials with HF in the presence of a catalyst.

8 Claims, No Drawings

PROCESS FOR PRODUCING 1,1,1,3,3-PENTAFLUORO-PROPANE AND/OR 1-CHLORO-3,3,3-TRIFLUOROPROPENE

FIELD OF THE INVENTION

The present invention relates to a manufacturing method for 1,1,1,3,3-pentafluoropropane and/or 1-chloro-3,3,3-trifluoropropene.

PRIOR ART 1,1,1,3,3-Pentafluoropropane is industrially important compound used as an HFC foaming agent, refrigerant or jetting agent, and is widely accepted as a fluoride that is kind to the environment since it does not destroy the ozone layer even when released into the air.

The following manufacturing methods for 1,1,1,3,3-pentafluoropropane are currently available.

Namely, the method described in WO 95/04022 first obtains 1,1,1,3,3,3-hexachloropropane by the addition reaction of carbon tetrachloride with vinylidene chloride. 1,1,1,3,3,3-hexachloropropane is fluorinated to give 1,1,1,3,3-pentafluoro-3-chloropropane. This is then reduced with hydrogen to obtain the desired product. Another method described in EPO 611744 uses 1,1,1,3,3-pentafluoro-2,3-dichloropropane and 1,1,1,3,3-pentafluoro-2, 3, 3-trichloropropane obtained in the previous process. These are reduced with hydrogen to give the desired product.

However, all of these manufacturing methods are not suited to industrial processes and are uneconomical because they require two different processes: a fluorinated process to obtain the precursor by fluorination of the chloride, and a reduction process to further reduce the precursor with hydrogen; and involve complicated steps.

Further, there are relatively new manufacturing methods using more simplified processes that first obtain 1,1,1,3,3-pentachloropropane by an addition reaction of carbon tetrachloride with vinyl chloride. 1,1,1,3,3-pentachloropropane is fluorinated using the following known methods: (1) fluorination by HF (hydrogen fluoride) in the liquid phase in the presence of a fluorination catalyst to give the desired product (WO 96/01797); and (2) fluorination by HF in the gaseous phase similarly in the presence of a fluorination catalyst to give the desired product (Japanese Patent Laid-Open No. 183,740/97).

In another method, 1,1,1,3,3-pentafluoropropane is produced as an objective product by fluorinating 1,1,3,3-tetrachloropropene and 1,3,3,3-tetrachloropropene. In this case, it is known that also 1-chloro-3,3,3-trifluoropropene is produced, which is a useful by-product.

OBJECT OF THE INVENTION

In the fluorination reaction of 1,1,1,3,3-pentachloropropane as described here, a Lewis acid catalyst such as an antimony halogenide or a halogenochromium oxide is generally used as a catalyst.

However, although the aforementioned reaction in the liquid phase gives good selectivity in the HF solvent only in the early step, as the reaction proceeds the catalyst slowly deactivates, and so it does not give the desired product in a short time. To recover the reaction, superfluous work is required, such as additional supplementation of the catalyst and treatment to regenerate the catalyst.

Further as the reaction proceeds, in addition to the deactivation of the catalyst, organic substances that have high boiling points accumulate in the reactor and it has been observed that these significantly inhibit the reaction.

Also in the reaction in the gaseous phase described above, since the activity of the catalyst is significantly reduced by water contained in the material and the HF, the progress of the reaction i s significantly inhibited. Also a high reaction temperature and continuous contact time between the catalyst and the gas must be maintained to achieve the desired conversion rate. For these reasons, it is impossible to avoid increases in running costs.

The present invention was studied from these stated viewpoints with the following aims in fluorinating specific organic chlorides as materials, which are represented by 1,1,1,3,3-pentachloropropane, with HF in the presence of a catalyst: providing a continuously efficient manufacturing method for 1,1,1,3,3-pentafluoropropane and/or 1-chloro-3,3,3-trifluoropropene; simultaneously preventing deactivation of the catalyst; and preventing the reaction from being inhibited by the accumulation of organic substances with high boiling points.

CONSTITUTION OF THE INVENTION

A manufacturing method for 1,1,1,3,3-pentafluoropropane and/or 1-chloro-3,3,3-trifluoropropene by the present invention is characterized by using all dehydrated materials and HF in order to obtain the objective products by fluorinating one or more of the materials selected from 1,1,1,3,3-pentachloropropane, 1,1,3,3-tetrachloropropene and 1,3,3,3-tetrachloropropene with HF in the presence of a catalyst. One of the intended products, 1-chloro-3,3,3-trifluoropropene may be used as the starting material for another intended product, 1,1,1,3,3-pentafluoropropane.

As described above, if water is removed from the materials and the HF before submitting them to the reaction, phenomena such as deactivation of the catalyst and accumulation of organic substances with high boiling points can be effectively controlled as described later, and useful 1,1,1,3,3-pentafluoropropane and/or 1-chloro-3,3,3-trifluoropropene can be manufactured continuously and efficiently.

By intense investigations on factors causing the aforementioned deactivation of the catalyst, the present inventors could find that a primary factor in the deactivation of said catalysts was the water contained in said materials and HF, especially the presence of water in the materials, because of the reaction with the catalysts. In addition, water in said HF and materials chemically reacts with the materials themselves under the reaction condition of the fluorination to generate organic substances with high boiling points. These substances slowly accumulate in the reactor to significantly inhibit the fluorination reaction, obstructing the continuous production of the intended products.

Thus, for a continuous and smooth fluorination reaction of said materials, before submitting said materials and HF to the reaction, it is necessary to remove water as much as possible from them, preferably to remove it about completely or to achieve a substantially anhydrous state, if possible.

Water inevitably becomes mixed in the materials and HF during the processes of manufacture and handling, and removal of this water to a high level of a few ppm is difficult using conventional techniques.

The present inventors found, as the results of repeated trial-and-error experiments to precisely investigate methods of dehydration, that the most effective method is to apply highly adsorbable zeolite to said materials and to use a distillation method for the HF.

Industrial Application

According to the manufacturing method of the present invention, when fluorinating three of said materials, which are typically represented by 1,1,1,3,3-pentachloropropane, with HF in the presence of a catalyst, more than sufficient water can be removed before submitting them to the reaction, preventing unwanted phenomena such as the deactivation of the catalyst by the water and the accumulation of organic substances with high boiling points as described previously. Thus, industrially important 1,1,1,3,3-pentafluoropropane and/or 1-chloro-3,3,3-trifluoropropene can be manufactured continuously and efficiently in a smooth fluorination reaction.

EXAMPLE

Hereinafter, the present invention will be described more specifically.

In the present invention, the material for the fluorination reaction with HF is selected from 1,1,1,3,3-pentachloropropane and 1,1,3,3-tetrachloropropene and 1,3,3,3-tetrachloropropene, either alone or as a mixture of two or more of them.

Incidentally, in the present invention, 1-chloro-3,3,3-trifluoropropene which is one of the intended products can be used as the starting material for the 1,1,1,3,3-pentafluoropropane which is another intended product.

The materials and HF must undergo a dehydration process before being submitted to the reaction. This can be done at any time before submitting these materials and HF to the reaction, either before or after receipt of them.

Accordingly, both the material that has undergone a dehydration process before and after receipt can be submitted to the reaction.

In dehydrating said materials, it is preferable to use zeolite as the dehydrating agent. The zeolite may be in any form, for example, powder, granule and another particle. The degree of dehydration should be controlled to not more than 20 ppm of water in the materials, and preferably be controlled to not more than 10 ppm.

Herein, when dehydrating, there are no specific conditions for bringing zeolite into contact with said materials; however, it is more efficient to arrange for said materials in the gaseous or liquid state to flow into a container charged with zeolite.

Distillation can be used to dehydrate said materials; however, since these types of materials are likely to thermally decompose, the distillation must be done under reduced pressure, so that it is not industrially expedient.

On the other hand, distillation is preferably used to dehydrate the HF. The degree of the dehydration for the HF is preferably controlled to not more than 10 ppm, and more preferably to not more than 5 ppm.

However, the phenomenon of deactivation of the fluorination catalyst by the water in the HF is also described in the above publication (WO 96/01795), There it states that water in the HF should be controlled to not more than 0.05%, and preferably to not more than 0.02% to prevent deactivation. In any case, the upper limit of the water content is incomparably larger than that in the present invention. Since the upper limit of the water content in the present invention is 10 ppm, only the HF defined in the present invention can be said to be "practically anhydrous".

In the fluorination reaction of the present invention, a catalyst is usually used. Although conventional catalysts in this field may be used, it is preferable to use a fluorination catalyst containing halogenides of one or more elements selected from antimony, niobium and tantalum, and fluorinated chromium oxide and fluorinated aluminum oxide.

Fluorinating said materials with HF in the presence of said specified catalyst, 1-chloro-3,3,3-trifluoropropene, which is another intended product, is produced in considerable amounts, and by separately fluorinating it or by recycling it to said fluorination reaction, the main intended product 1,1,1,3,3-pentafluoropropane can be obtained again. Here, said specified catalysts are fluorinated chromium oxide and fluorinated aluminum oxide.

In the present invention, when performing the fluorination reaction in the presence of the fluorination catalyst, the charged mol. ratio of said HF to material is usually 3–20, and preferably 5–10.

The reaction temperature is usually 50–350° C., and preferably 80–300° C., and the reaction time is usually 1 sec–30 min.

Now, the present invention will be illustrated more specifically based on Examples. However, the present invention is not limited to those Examples.

Example 1

Initially dehydration treatments of the material were variously performed using zeolite before submitting the material to the fluorination reaction, as are illustrated in the following Preparation Examples 1 to 9.

Preparation Example 1

50 g of molecular sieve 4A as the dehydrating agent was added to 500 g of 1,1,1,3,3-pentachloropropane and stirred mildly at room temperature for 12 hrs.

The difference in the water content of the material before and after addition of this dehydrating agent was measured using the Karl Fischer method. The results are shown in Table 1 as described later.

Preparation Example 2

Except for the use of molecular sieve 3A substituted for molecular sieve 4A, a dehydration process similar to Preparation Example 1 above was used, and the water content was measured. The results are shown in Table 1.

Preparation Example 3

Except for the use of molecular sieve 13X substituted for molecular sieve 4A, a dehydration process similar to Preparation Example 1 above was used, and the water content was measured. The results are shown in Table 1.

Preparation Example 4

Except for the use of molecular sieve 10X substituted for molecular sieve 4A, a dehydration process similar to Preparation Example 1 above was used, and the water content was measured. The results are shown in Table 1.

TABLE 1

| Water in Material | Before Addition of Dehydrating Agent | After Addition of Dehydrating Agent |
| --- | --- | --- |
| Preparation Example 1 | 130 ppm | 9 ppm |
| Preparation Example 2 | 126 ppm | 11 ppm |

TABLE 1-continued

| Water in Material | Before Addition of Dehydrating Agent | After Addition of Dehydrating Agent |
|---|---|---|
| Preparation Example 3 | 132 ppm | 8 ppm |
| Preparation Example 4 | 123 ppm | 13 ppm |

Preparation Example 5

Except for the use of 1,1,3,3-tetrachloropropene substituted for 1,1,1,3,3-pentachloropropane, a dehydration process similar to Preparation Example 1 above was used, and the water content was measured. The results are shown in Table 2 as described later.

Preparation Example 6

Except for the use of 1,1,3,3-tetrachloropropene substituted for 1,1,1,3,3-pentachloropropane, a dehydration process similar to Preparation Example 2 above was used, and the water content was measured. The results are shown in Table 2.

Preparation Example 7

Except for the use of 1,1,3,3-tetrachloropropene substituted for 1,1,1,3,3-pentachloropropane, a dehydration process similar to Preparation Example 3 mentioned above was used, and the water content was measured. The results are shown in Table 2.

Preparation Example 8

Except for the use of 1,1,3,3-tetrachloropropene substituted for 1,1,1,3,3-pentachloropropane, a dehydrating process similar to Preparation Example 4 mentioned above was used, and the water content was measured. The results are shown in Table 2.

TABLE 2

| Water in Material | Before Addition of Dehydrating Agent | After Addition of Dehydrating Agent |
|---|---|---|
| Preparation Example 5 | 73 ppm | 7 ppm |
| Preparation Example 6 | 69 ppm | 10 ppm |
| Preparation Example 7 | 71 ppm | 8 ppm |
| Preparation Example 8 | 71 ppm | 12 ppm |

Preparation Example 9

50 g of molecular sieve 4A was added to a 500 g mixture of 80 mol% of 1,1,3,3-tetrachloropropene and 20 mol% of 1,3,3,3-tetrachloropropene and stirred mildly at room temperature for 12 hrs.

The difference in the water content of the material before and after addition of this dehydrating agent was measured using the Karl Fischer method. The results show that the value was 150 ppm before addition of the dehydrating agent and 8 ppm after addition.

The fluorination reaction of the material was then carried out according to the following procedures.

Initially, to prepare the fluorination catalyst, 15 g (0.05 mol) of antimony pentachloride was charged into a 500 ml volume autoclave coated with polytetrafluoroethylene, then cooled in dry ice, a further 220 g (11 mol) of HF was added, thereafter the temperature was slowly elevated to room temperature. Subsequently, the temperature in the reactor was elevated to 80° C., removing the generated hydrochloric acid.

Then the 1,1,1,3,3-pentachloropropane (water content of 10 ppm), treated to dehydrate it according to Preparation Examples 1 to 4, was charged at a rate of 60 g/hr into this reactor and the HF (water content of 10 ppm), treated to dehydrate it separately using the distillation method, was charged at a rate of about 35 g/hr. With the pressure in the reactor controlled to around 10 kg/cm$^2$, the reaction was continued for 20 hr, removing the generated hydrochloric acid and the 1,1,1,3,3-pentafluoropropane.

After halting the introduction of the material and HF and further reacting for 3 hrs, the pressure was gradually reduced to exclude compounds with low boiling points in the reactor from the system. Thereafter, aqueous hydrochloric acid was added to the reactor and the residual compounds with high boiling points were extracted with dichloromethane. Dichloromethane from this extract was evaporated to give 0.21 g of organic tar substances.

Comparative Example 1

Except for the use of nondehydrated 1,1,1,3,3-pentachloropropane (water content of 130 ppm) as the material and nondehydrated HF (water content of 100 ppm), a fluorination reaction similar to Example 1 was carried out. After the reaction, the weight of the residual organic tar substances was 2.5 g.

Example 2

Except for the use of dehydrated 1,1,3,3-tetrachloropropene as in Preparation Example 6 substituted for the dehydrated 1,1,1,3,3-pentachloropropane described above, and with the charging rate controlled to 50 g/hr, a fluorination reaction similar to Example 1 described above was carried out. After the reaction, 0.42 g of organic tar substances was obtained.

Comparative Example 2

Except for the use of nondehydrated 1,1,1,3,3-pentachloropropane (water content of 130 ppm) and nondehydrated HF (water content of 100 ppm) in place of the dehydrated 1,1,1,3,3-pentachloropropane and HF described above, a fluorination reaction similar to Example 1 described above was carried out. After the reaction, 3.6 g of organic tar substances was obtained.

Example 3

Fluorinated chromium oxide was obtained through the following procedures: precipitating chromium hydroxide by the addition of aqueous ammonia from aqueous chromium nitrate; obtaining chromium oxide by thermally treating this; and further bringing hydrogen fluoride into contact with the chromium oxide.

Then, the fluorinated chromium oxide was charged as a catalyst into a Hastelloy C reaction tube, 20 mm in internal diameter and 700 mm in length, and elevated to a temperature of 250° C. in a current of nitrogen.

Then, after stopping the nitrogen supply, the dehydrated 1,1,1,3,3-pentachloropropane (water content of 10 ppm) was gasified and charged at a flow rate of 20 cc/min into the same reaction tube, and simultaneously dehydrated HF (water content of 10 ppm) was gasified and charged at a flow rate of 200 cc/min.

The generated gas was washed with water, dried, and then submitted to gas chromatography. This gas proved to be a mixed gas with the following composition.

| | |
|---|---|
| 1,1,1,3-tetrafluoro-2-propene | 2.1% |
| 1,1,1,3,3-pentafluoropropane | 5.0% |
| 1,1,1-trifluoro-3-chloropropene | 92.9% |

Thus, the generated gas was obtained and washed with water to remove hydrogen chloride, and dried. Preserving the same reaction conditions as above, the generation gas (mixed gas with 1,1,1-trifluoro-3-chloropropene as the main component) was introduced into the reactor at a flow rate of 20 cc/min and the hydrogen fluoride at a flow rate of 200 cc/min, and reacted again.

The generated gas was obtained and washed with water and then submitted to gas chromatography. The generated gas proved to be a mixed gas having the following composition.

| | |
|---|---|
| 1,1,1,3-tetrafluoro-2-propene | 23.4% |
| 1,1,1,3,3-pentafluoropropane | 52.3% |
| 1,1,1-trifluoro-3-chloropropene | 24.3% |

Comparative Example 3

Except for the use of nondehydrated 1,1,1,3,3-pentachloropropane (water content of 130 ppm) as the material and nondehydrated HF (water content of 100 ppm), a fluorination reaction similar to Example 3 described above was carried out.

The generated gas was washed with water, dried, and then submitted to gas chromatography. This generated gas proved to be a mixed gas having the following composition.

| | |
|---|---|
| 1,1,1,3-tetrafluoro-2-propene | 1.9% |
| 1,1,1,3,3-pentafluoropropane | 4.5% |
| 1,1,1-trifluoro-3-chloropropene | 81.2% |
| 1,1,1-trifluoro-3,3-dichloropropane | 7.6% |
| 1-fluoro-1,1,2,2-tetrachloropropane | 4.8% |

What is claimed is:

1. A manufacturing method for 1,1,1,3,3-pentafluoropropane and/or 1-chloro-3,3,3-trifluoropropene using dehydrated materials and hydrogen fluoride submitted to a reaction system when fluorinating one or more said materials selected from 1,1,1,3,3-pentachloropropane, 1,1,3,3-tetrachloropropene and 1,3,3,3-tetrachloropropene with hydrogen fluoride in the present of a catalyst, wherein water contained in said materials is controlled to not more than 20 ppm and water contained in said hydrogen fluoride is controlled to not more than 10 ppm.

2. A manufacturing method for 1,1,1,3,3-pentafluoropropane and/or 1-chloro-3,3,3-trifluoropropene as claimed in claim 1 wherein said materials and/or hydrogen fluoride from which water is removed beforehand are submitted to said reaction system.

3. A manufacturing method for 1,1,1,3,3-pentafluoropropane and/or 1-chloro-3,3,3-trifluoropropene as claimed in claim 1, wherein said materials and/or hydrogen fluoride after dehydration are submitted to said reaction system.

4. A manufacturing method for 1,1,1,3,3-pentafluoropropane and/or 1-chloro-3,3,3-trifluoropropene as claimed in any one of claims 1–3 wherein a fluorination catalyst containing halogenides of one or more elements selected from antimony, niobium and tantalum is used as said catalyst.

5. A manufacturing method for 1,1,1,3,3-pentafluoropropane and/or 1-chloro-3,3,3-trifluoropropene as claimed in any one of claims 1–3 wherein a fluorinated chromium oxide catalyst and/or a fluorinated aluminum oxide catalyst are used as said catalyst.

6. A manufacturing method for 1,1,1,3,3-pentafluoropropane and/or 1-chloro-3,3,3-trifluoropropene as claimed in claim 3 wherein a dehydrating agent is used for said dehydrating treatment of said materials and said hydrogen fluoride.

7. A manufacturing method for 1,1,1,3,3-pentafluoropropane and/or 1-chloro-3,3,3-trifluoropropene as claimed in claim 6 wherein zeolite is used as said dehydrating agent.

8. A manufacturing method for 1,1,1,3,3-pentafluoropropane and/or 1-chloro-3,3,3-trifluoropropene as claimed in claim 3 wherein a distillation method is used for dehydrating said hydrogen fluoride.

* * * * *